(12) United States Patent
Hafner

(10) Patent No.: US 8,100,906 B2
(45) Date of Patent: Jan. 24, 2012

(54) ELECTROSURGICAL INSTRUMENT

(75) Inventor: Dieter Hafner, Tübingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 1159 days.

(21) Appl. No.: 11/886,839

(22) PCT Filed: Mar. 21, 2006

(86) PCT No.: PCT/EP2006/002605
§ 371 (c)(1),
(2), (4) Date: Sep. 21, 2007

(87) PCT Pub. No.: WO2006/100046
PCT Pub. Date: Sep. 28, 2006

(65) Prior Publication Data
US 2009/0036887 A1 Feb. 5, 2009

(30) Foreign Application Priority Data

Mar. 24, 2005 (DE) .......................... 10 2005 013 847

(51) Int. Cl.
*A61B 18/18* (2006.01)
(52) U.S. Cl. ................ 606/51; 606/45; 606/15; 606/49; 606/52
(58) Field of Classification Search ............... 606/51–52
See application file for complete search history.

(56) References Cited

U.S. PATENT DOCUMENTS

| | | | | |
|---|---|---|---|---|
| 2,484,059 A | * | 10/1949 | Wallace | 606/46 |
| 3,732,858 A | * | 5/1973 | Banko | 600/566 |
| 3,945,375 A | * | 3/1976 | Banko | 600/104 |
| 4,976,711 A | * | 12/1990 | Parins et al. | 606/48 |
| 5,078,717 A | | 1/1992 | Parins et al. | |
| 5,354,296 A | | 10/1994 | Turkel | |

(Continued)

FOREIGN PATENT DOCUMENTS

| EP | 448857 A1 | 10/1991 |
|---|---|---|
| EP | 795301 B1 | 9/1997 |
| WO | WO-99/37228 | 7/1999 |

OTHER PUBLICATIONS

International Preliminary Report on Patentability (2 pages).
Written Opinion (4 pages).

*Primary Examiner* — Linda Dvorak
*Assistant Examiner* — Jaymi Della
(74) *Attorney, Agent, or Firm* — Dickstein Shapiro LLP

(57) ABSTRACT

The invention relates to an electrosurgical instrument for cutting and/or coagulating a tissue to be treated, comprising at least one cutting electrode for conducting a high-frequency ("HF") current through the tissue for carrying out a cutting process and comprising power supply devices for supplying the HF current at least to the cutting electrode. The design of the electrosurgical instrument is improved so that the cutting process can be carried out with an increased reliability while prolonging the serviceable life of the cutting electrode at the same time. To this end, the cutting electrode is mounted on the electrosurgical instrument in a manner that enables it to rotate about a rotation axis and comprises at least one cutting area which is provided in the form of a helical curve or similar three-dimensional curve running around the rotation axis and which is arranged in such a manner that when the cutting electrode rotates about the rotation axis it is active over its length in sections on the tissue when a section falls below a defined minimum distance from the tissue and/or is located within a defined window area.

11 Claims, 5 Drawing Sheets

U.S. PATENT DOCUMENTS

| | | | |
|---|---|---|---|
| 5,527,331 A | * | 6/1996 | Kresch et al. .................. 606/170 |
| 6,007,533 A | * | 12/1999 | Casscells et al. ............... 606/45 |
| 2002/0049439 A1 | | 4/2002 | Mulier et al. |
| 2003/0023287 A1 | | 1/2003 | Edwards et al. |

* cited by examiner

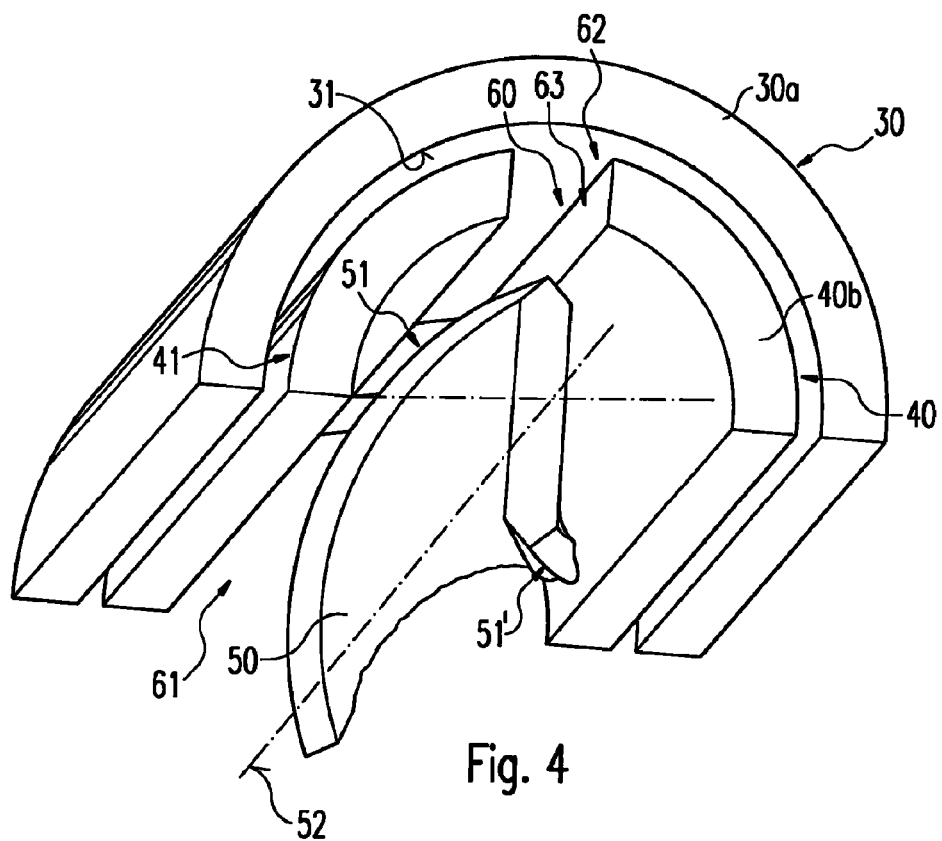
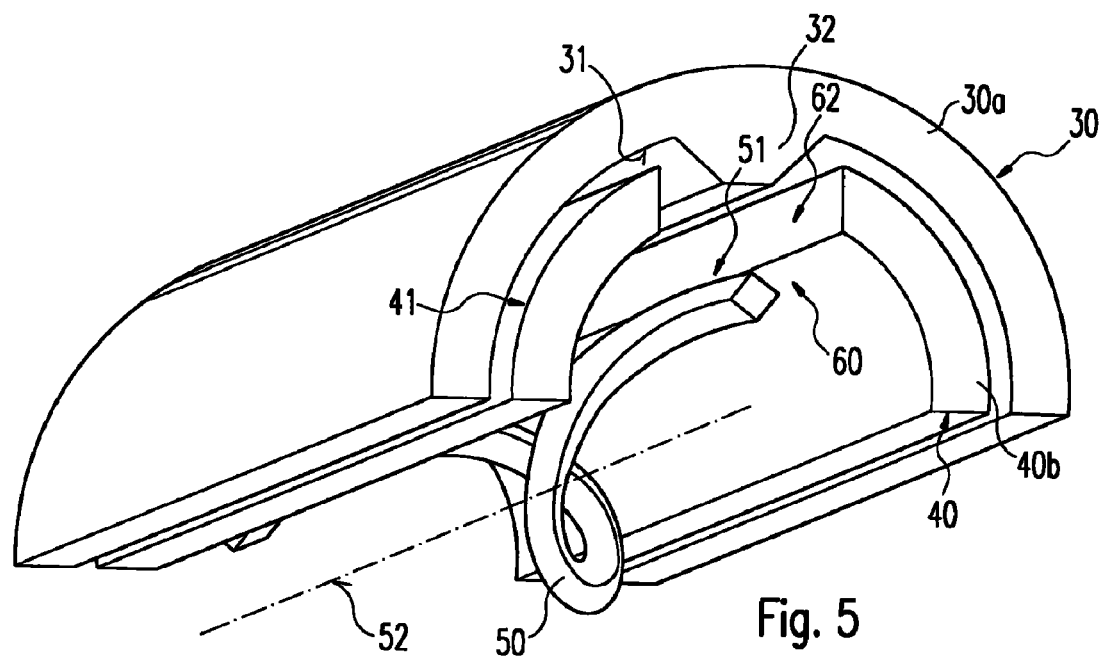

ELECTROSURGICAL INSTRUMENT

CROSS-REFERENCE TO RELATED APPLICATIONS

This application claims priority to International Patent Application No. PCT/EP2006/002605, filed on Mar. 21, 2006, which claims priority to German Patent Application Ser. No. 10 2005 013 847.0, filed Mar. 24, 2006. Each of the above listed applications are herein incorporated by reference in their entirety.

FIELD OF THE INVENTION

The invention relates to an electrosurgical instrument.

BACKGROUND OF THE INVENTION

Electrosurgical instruments have been used in high-frequency surgery for many years to coagulate or to cut biological tissue. In the case of a coagulation, a high-frequency ("HF") current is conducted through the tissue to be treated so that it changes due to protein coagulation and dehydration. In this case, the tissue contracts such that the vessels are closed and bleeding is stopped. A cutting process requires a high current density so that the tissue is completely cut through by an explosive evaporation of the tissue fluid and an associated ripping open of the cell membranes.

Both monopolar and bipolar techniques are used for the thermal treatment of biological tissue.

In the case of the monopolar technique, the HF current supplied by a HF generator to the electrosurgical instrument is applied into the tissue to be treated by means of an active electrode, the current path through the body of a patient leading to a passive neutral electrode and from there back to the HF generator. A high current density per surface unit is provided for treatment at the active electrode, while in the case of the neutral electrode the current density per surface unit is significantly reduced in comparison to the active electrode. This can be achieved by designing the neutral electrode with a correspondingly large surface. Monopolar cutting is particularly suitable for large cuts, for example, to cut through fat tissue.

The bipolar technique is used when the HF current should be applied with high precision. Bipolar instruments generally have two clamping parts connected to one another in an articulated manner, handle devices for handling the clamping parts being provided at their proximal ends. Electrode parts for conducting the HF current from the HF generator through the tissue to be treated are located at distal ends of the clamping parts. To this end, the electrode parts can be connected via power supply devices to the HF generator. The electrode parts are usually designed in such a manner that they are also suitable for holding and clamping the tissue to be treated. Due to the short current path between the electrode parts of the bipolar instrument, the current path can be better calculated than in the case of monopolar arrangements since it does not run long distances through the body of the patient.

WO 99/37228 discloses a bipolar coagulation and cutting device for endoscopic surgery. Two branches are provided which can be moved by means of an axially displaceable tube part. The branches have flat coagulation electrodes which are respectively formed on the inside with a hole area and which are opposite one another at distal ends in order to hold and coagulate a tissue to be treated with these. Moreover, a rod-shaped cutting electrode is provided which can also be moved by means of the tube part and which attacks the clamped tissue between the coagulation electrodes through the hole area. As a result of a successive linear displacement of the tube part, the cutting electrode—similar to the cut made by scissors—moves ever closer to the tissue to be treated until it has completely covered the desired cutting line.

The cutting area of the cutting electrode of an electrosurgical instrument is both in the case of the monopolar and in the case of the bipolar technique, as shown with WO 99/37228, constantly exposed to high stresses since a high current density required for the cutting process at the electrode promotes wear of the electrode.

Other electrosurgical instruments provide cutting electrodes of extremely small design (e.g. needle electrode) such that a simultaneous coagulation cannot be sufficiently carried out due to small coagulation surfaces. Particularly in the case of hollow organs such as blood vessels, it is thus very difficult to perform a targeted thermofusion.

Electrosurgical instruments are often formed with a cutting edge which must be activated mechanically. After successful coagulation, the treated tissue can be completely cut through by means of the cutting edge. The force which has to be applied by the surgeon in this case during cutting also brings about a high degree of wear of the cutting edge with the result that the quality of the cut is significantly reduced after only a short time. The cutting electrode must therefore be replaced on a frequent basis, which is often difficult as a result of relatively complex mechanics. In some cases, it may even no longer be possible to use the entire electrosurgical instrument and it must therefore be completely replaced.

SUMMARY OF THE INVENTION

The object of the invention is therefore to improve an electrosurgical instrument of the type mentioned above so that the cutting process can be carried out with an increased reliability while prolonging the serviceable life of the cutting electrode at the same time.

In particular, the object is achieved by an electrosurgical instrument for cutting and/or coagulating a tissue to be treated comprising at least one cutting electrode for conducting a HF current through the tissue for carrying out a cutting process and comprising power supply devices for supplying the HF current at least to the cutting electrode, the cutting electrode being mounted on the electrosurgical instrument in a manner that enables it to rotate about a rotation axis and comprising at least one cutting area which is provided in the form of a helical curve or similar three-dimensional curve running around the rotation axis and which is arranged in such a manner that when the cutting electrode rotates about the rotation axis it is active over its length in sections on the tissue when this section falls below a defined minimum distance from the tissue and/or is located within a defined window area.

A key point of the invention lies in the fact that, due to the configuration of the cutting electrode, a large cutting area is available, wherein only sections of the cutting area are respectively used due to the rotation of the cutting electrode. This means that a voltaic arc can only be generated between individual sections of the cutting area and the tissue to be treated and a successive cutting process can thus be performed. This means that any wear can be distributed to the individual sections so that the serviceable life of the cutting electrode is lengthened. In the case of cutting with high-frequency alternating current, a cut through the tissue is only possible if the electrical voltage between the active electrode and the tissue is so large that electric voltaic arcs ignite. If the cutting area thus runs over the tissue, the voltaic arcs ignite everywhere where the distance between the cutting area and the tissue is sufficiently small. The area of the cutting area which enables ignition of the voltaic arcs is therefore the active section of the cutting area.

Due to the configuration of the cutting electrode comprising the active section, the generation of a linear cut on the tissue to be treated is enabled by means of the rotation of the cutting electrode. To carry out the linear cutting movement, the rotational movement is ultimately used and a reduction (downwards) is thus generated in the case of a sufficiently high number of turns per unit of length. Particularly precise cuts can therefore be achieved, which is above all advantageous in the case of very short cut lengths. Since the three-dimensional curve for forming the cutting area is ultimately defined by a certain number of turns, the cutting speed, i.e. the speed at which the active sections move across the tissue, can also be adjusted using the number of turns. The cutting speed of the active sections is inversely proportional to the number of turns per unit of length with the speed of rotation remaining the same. The progress of the individual voltaic arcs over the entire length of the cut also becomes slower in this case due to the helical reduction effect.

A first preferred embodiment provides that the cutting electrode encompasses a helical line-shaped rod element, the cutting area is formed as a helical curve on the rod element and the section of the cutting area along the helical curve runs along the rod element when the cutting electrode rotates. The helical curve for the cutting area is particularly easy to produce in this manner. Therein, the rod element can be wound in such a manner that the section runs along a surface of the at least one cutting area or along an edge. If the section runs along the edge, a higher current density can be achieved on said section.

A further preferred embodiment provides that the cutting electrode encompasses a twisted surface element on whose edges two cutting areas are formed as helical curves and the section of the cutting areas along the helical curves runs along the surface element when the cutting electrode rotates. A cutting area which runs in a helical line shape can thus be formed in a particularly simple manner. Moreover, the cutting electrode formed in this manner is extremely stable and withstands mechanical stresses to a high level.

The rod element described above can also be twisted and arranged in such a manner that four cutting areas are ultimately formed as helical curves and the respective active section of the cutting areas along the helical curves runs along the rod element when the cutting electrode rotates.

The cutting electrode can in principle be formed as any three-dimensional curve such that the three-dimensional curve describes, for example, an envelope of a cone or a similar geometric figure.

The cutting electrode is preferably formed comprising at least one turn, preferably comprising precisely one turn. Precisely one active section of the cutting area is thus in interaction with the tissue and the cut can be carried out precisely and in an understandable manner.

Alternatively, the cutting electrode can also be formed as a cylindrical hollow body or as a rod solid material on which the helical line-shaped cutting area is arranged. Therein, the hollow body or the solid material itself can be provided in an electrically insulating manner. If the hollow body or the solid material is formed from electrically conductive material comprising an insulation layer provided on the surface area, the helical line-shaped cutting area can thus be exposed by partial removal of the insulation layer, e.g. by milling or via a cutting process performed by means of voltaic arcs. A cutting electrode formed in this manner is extremely stable and resistant to wear, particularly when using a solid material.

Two branches are preferably provided which are connected to one another in an articulated manner and which can be activated according to a clamping or cutting tool and thus form a retaining device comprising respectively at least one holding element on the branches for holding the tissue to be treated. The clamping of the tissue requires its fixing so that a precise cut can be achieved in this manner. Due to the fact that the tissue is clamped between the holding elements, the retaining device must be formed in such a manner that the cutting electrode can interact in an unhindered manner with the clamped tissue to be treated. Cutting by means of the HF current is substantially performed in a contact-free manner by means of cutting sparks, i.e. by means of voltaic arcs, so that the cutting electrode must be arranged so as to only be able to rotate about itself and must otherwise be mounted in a stationary manner. At least one of the holding elements therefore comprises a receiving/passage area for the cutting electrode, a receiving area being provided for mounting of the cutting electrode in or on the holding elements, while a passage area enables the cutting spark to access the tissue to be treated. This means that the voltaic arc can be generated across the passage area between the cutting electrode and the tissue clamped in the retaining device. If the cutting electrode is now rotated about the rotation axis, the active section of the cutting area migrates along the passage area and the clamped tissue is cut through.

The receiving/passage area is advantageously formed in such a manner that it comprises the defined window area. If, for example, the HF cutting current or the voltage is controlled such that sections of the cutting area are active on the tissue when they fall below a defined minimum distance to the tissue, the receiving/passage area must be designed in such a manner that an obstruction of the cutting electrode is prevented by the retaining device. At the same time, a sufficient fixing of the tissue must be ensured. No further requirements must be placed on the configuration of the receiving/passage area in this case. If, however, the action of the active section of the cutting area is dependent on the configuration, in particular on the size of the receiving/passage area, this is preferably formed as the defined window area. The defined window area only exposes the tissue area on which the cut is to be carried out. The remaining tissue is covered by the holding element which specifies the window area such that current cannot be applied there. When the cutting electrode rotates, the active section migrates along the window area. The defined window area enables extremely precise cut guidance because the cut area is exactly delimited. Moreover, the performance of the cut is largely independent of other parameters such as e.g. the set current strength or voltage as a function of the distance of the cutting area from the tissue to be treated (naturally within certain limits).

In practical use, the retaining device comprises a first electrode and a second electrode for conducting a coagulation current for the coagulation process through the tissue as holding elements respectively on the branches so that the electrosurgical instrument is primarily provided as a bipolar arrangement. Before the actual cutting process, the clamped tissue, e.g. a vessel, can be coagulated first and subsequently cut through by means of the cutting electrode. The cutting electrode can then interact with one of the coagulation electrodes during the cutting process so that the cutting and corresponding coagulation electrode in turn form a bipolar arrangement. An interaction of the cutting electrode with the neutral electrode already described above is also possible.

The receiving/passage area preferably comprises an insulation layer at least on surface areas facing in the direction of the cutting electrode so that the electrode which is opposite the electrode comprising the receiving/passage area and the cutting electrode form a bipolar arrangement during the cutting process. It is thus ensured that no interaction between the electrode comprising the receiving/passage area and the cutting electrode occurs during the cutting process.

If the retaining device comprises two coagulation electrodes, the first electrode, the second electrode and the cutting electrode are e.g. arranged relative to one another in such a manner that the second electrode is formed between the first electrode and the cutting electrode. This means that the cutting electrode extends below or outside the retaining device in this case. The tissue to be treated can there be clamped by means of the first and the second electrode and can be coagulated in a first step. During the coagulation process, the cutting electrode is inactive. In a second step, a cutting process is carried out by means of the cutting electrode on the coagulated tissue. In order to enable access for the cutting electrode, at least the second electrode comprises the receiving/passage area. The surface areas of the receiving/passage area which are formed in the direction of the cutting electrode also comprise the insulation layer. An interaction between the cutting electrode and the second electrode, for example, by uncontrolled sparking, is prevented. The first electrode and the cutting electrode form a bipolar arrangement during the cutting process. In the case of this embodiment too, the receiving/passage area is preferably formed as a defined window area.

Of course, the cutting electrode can also be arranged above the retaining device so that the first electrode comprises the receiving/passage area and/or the window area.

Alternatively, it is possible that the cutting electrode is mounted within one of the coagulation electrodes. To this end, the first electrode, the second electrode and the cutting electrode are arranged relative to one another in such a manner that cutting electrode is formed between the first electrode and the second electrode. In this embodiment, the cutting electrode is therefore accommodated between the coagulation electrodes (or between the holding elements) and is thus protected, for example, from mechanical stress. To this end, either the first electrode or the second electrode comprises the receiving/passage area, the receiving/passage area also being provided here with the insulation layer on the surface areas in the direction of the cutting electrode so that the electrode opposite the receiving/passage area and the cutting electrode form the bipolar arrangement during the cutting process. The receiving/passage area is preferably formed in such a manner that it is provided as the defined window area. Precise cut guidance is thus ensured.

In a further preferred embodiment, the retaining device comprises an electrode as a holding element and a further electrically insulating holding element, the electrode and the cutting electrode being arranged relative to one another in such a manner that they form a bipolar arrangement during the cutting process. All the above-mentioned variants can also be produced in the case of this embodiment. This means that the cutting electrode can be arranged between the holding elements or also above or below the same. If a holding element is formed as an electrically insulating element, no explicit insulation layer later needs to be provided between this element and the cutting electrode. This means that the receiving/passage area and/or the window area for the cutting electrode can be formed particularly easily.

By varying the dimensions of the passage area, in particular of the defined window area, various treatment possibilities can be realised. For example, a coagulation surface is widened by a narrower window area, in particular in the case of a configuration of the holding elements as coagulation electrodes. This ensures optimum coagulation of the tissue to be treated. On the contrary, moisture can be retained in the tissue to be treated during the coagulation process with a wider window area and a wider passage area so that a required cutting energy can be reduced.

Alternatively, it is possible to form the retaining device by means of two electrically insulating holding elements. The retaining device is then only used to clamp and fix the tissue to be treated, while a counter electrode to the cutting electrode is formed, for example, as a neutral electrode fastened to the patient.

A solution according to the invention provides that the holding element opposite the receiving/passage area comprises a protruding area in the direction of the receiving/passage area for conveying the tissue to be treated and/or for introducing the tissue to be treated into the receiving/passage area. This measures enables the cut guidance to be specified, for example, by improved guidance of the cutting spark. Moreover, moisture in the tissue remains for a longer time in the passage area so that the required cutting energy can be reduced.

A preferred embodiment provides that the holding elements respectively comprise at least one tensioning area in such a manner that, during clamping of the tissue, it is pretensioned between the holding elements and the cutting process can be carried out on the pretensioned tissue by means of the cutting electrode. The tissue is pulled, i.e. tightened, by the tensioning areas on both sides in the direction of their end areas. The tensioned tissue can be cut through more precisely and cleanly because fibres of the tissue align themselves transverse to a cutting direction and the tissue becomes thinner in this case.

The tensioning effect can be further strengthened by a surface profile on the holding elements. To this end, the profile is preferably formed on end areas at least on a tensioning area and additionally moves the tissue in a tensile direction defined by the tensioning areas or prevents a return of the tissue counter to this tensile direction.

The surface profile which supports the tensioning effect is preferably formed as a saw tooth profile. Teeth of the profile can, for example, be arranged in such a manner that they reach ever further into the tissue during the bringing together of the branches and carry this in the tensile direction. The tensioning in the tissue is thus significantly increased. However, it must be ensured that damage to the tissue is prevented by the profile so that the teeth are preferably formed as rounded knobs.

One of the tensioning areas is preferably curved in a convex manner at least in a first central section, the tensioning area opposite it is curved in a concave manner at least in a second central section. The tensioning areas thus fit into each other in a substantially positive-locking manner when the branches are brought together. As a result of the curved tensioning areas, a tensioning of the tissue is enabled in the simplest manner because this tissue is extended by the curved areas. As a result of the positive locking, the tissue is then securely locked between the branches in the tensioned state.

In order to enable the rotation of the cutting electrode, a rotational drive is assigned to the electrosurgical instrument. The rotation is thus carried out automatically without an operator having to pay attention thereto provided that this is e.g. an electrical drive. A mechanical drive is also conceivable. The drive is then e.g. formed in such a manner that it can be activated by means of a finger wheel formed on the electrosurgical instrument.

Further embodiments of the invention will become apparent from the subordinate claims.

BRIEF DESCRIPTION OF THE DRAWINGS

The invention is described further below with reference to exemplary embodiments which are explained in greater detail with reference to the figures. Herein

FIG. 4 shows a perspective view of a holding element and/or electrode arrangement according to a second preferred embodiment;

FIG. 5 shows a perspective view of a holding element and/or electrode arrangement according to a third preferred embodiment;

In the following description, the same reference numbers are used for identical parts and parts with an identical function.

DETAILED DESCRIPTION

Figure 1:
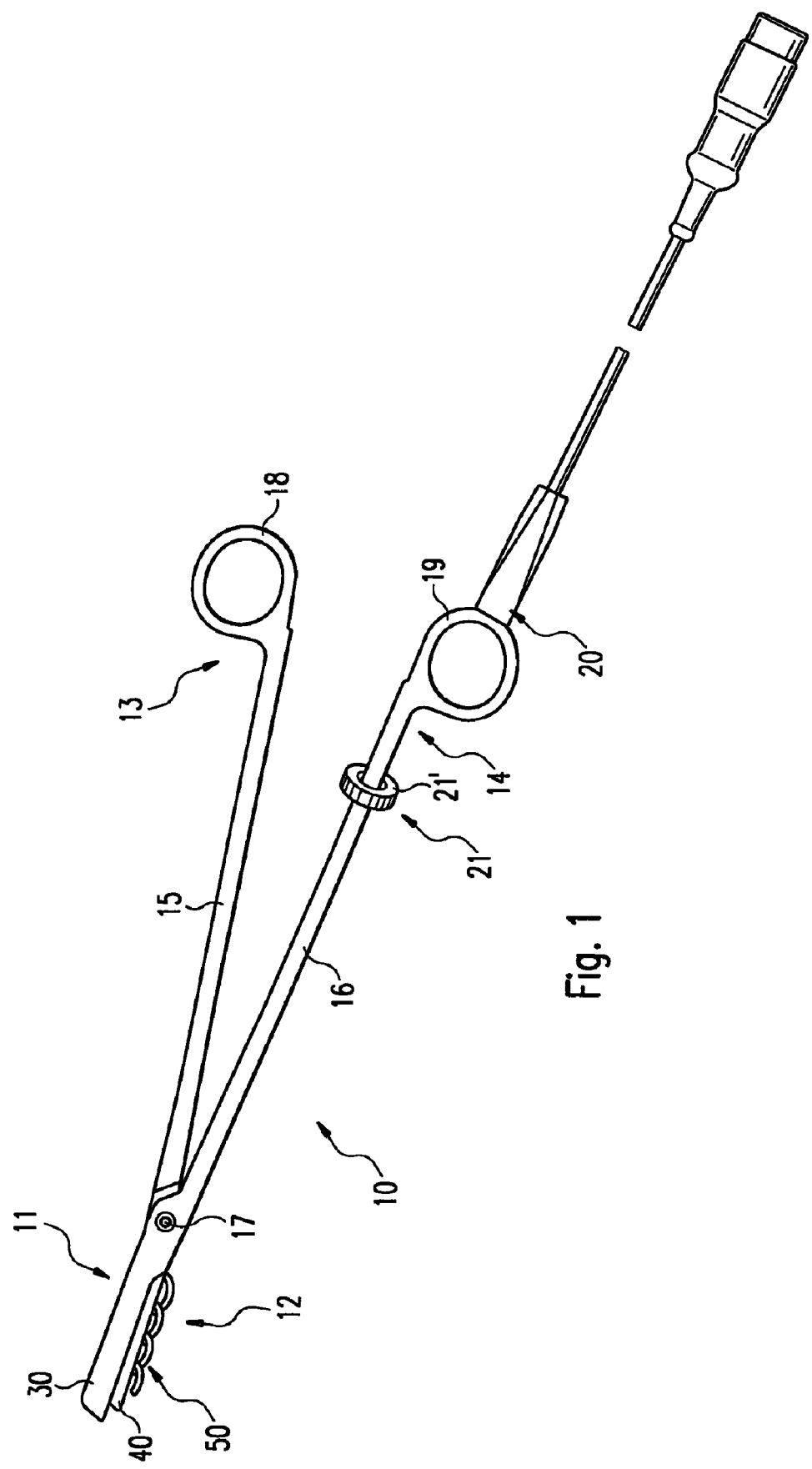
FIG. 1 shows a perspective view of an electrosurgical instrument comprising a holding element and/or electrode arrangement according to the invention in a first preferred embodiment.

FIG. 1 shows a perspective view of an electrosurgical instrument 10 comprising a holding element and/or electrode arrangement according to the invention in a first preferred embodiment. Instrument 10 is formed for engagement on the opened body and is provided for the treatment of biological tissue 80 (of FIG. 3). In the figure, two branches of electrosurgical instrument 10 are designated by reference numbers 15 and 16. Both branches 15, 16 are connected to one another by means of an axis 17 and can be swivelled about this. They comprise distal ends 11, 12 provided with a first holding element 30 and a second holding element 40, holding elements 30, 40 being opposite one another and being provided for holding and fixing the tissue to be treated. Moreover, a helical line-shaped cutting electrode 50 is provided which in this case is arranged below both holding elements 30, 40. Cutting electrode 50 is capable of rotating about a rotation axis so that a rotational drive 21 is preferably assigned to electrosurgical instrument 10. In this case, rotational drive 21 can be activated via a finger wheel 21' so that the operator can activate i.e. rotate cutting electrode 50, for example, manually. As a result of this configuration of cutting electrode 50, a large cutting area 51 (see, e.g., FIG. 2) formed along the helical curve is available, wherein only sections of cutting area 51 are respectively used due to the rotation of cutting electrode 50. This enables any wear to be distributed to the individual sections of the cutting area such that the serviceable lifetime of cutting electrode 50 is increased. This means that the serviceable lifetime is increased in comparison to conventional electrodes (e.g. needle electrode) by the migration of the stress point.

To carry out the linear cutting movement, the rotational movement is ultimately used and thus a reduction (downwards) is generated in the case of a sufficiently high number of turns per unit of length. Particularly precise cuts can therefore be achieved, which is above all advantageous in the case of very short cut lengths. Since the three-dimensional curve for forming the cutting area is ultimately defined by a certain number of turns, the cutting speed, i.e. the speed at which the active sections move across the tissue, can be set using the number of turns. The cutting speed of the active sections is inversely proportional to the number of turns per unit of length with the speed of rotation remaining the same. The progress of the individual voltaic arcs over the entire length of the cut becomes slower in this case due to the helical reduction effect. For a further explanation of cutting electrode 50, reference is made to the following description of the figures.

Moreover, handles 18, 19 are provided at respective proximal ends 13, 14 of electrosurgical instrument 10. Proximal end 14 of branch 16 ends in a power connection element or a power supply device 20 for connecting electrosurgical instrument 10 to a HF generator (not shown) which generates a HF voltage so that a HF current can, for example, be supplied through electrical lines (not shown) which run in instrument 10 at least to cutting electrode 50. Alternatively, it is possible to provide a power supply at both branches 15, 16.

In this embodiment, holding elements 30, 40 can be formed as coagulation electrodes so that a first coagulation electrode and a second coagulation electrode are opposite one another. This enables, prior to the cutting through of the fixed tissue, the coagulation thereof in that the coagulation electrodes form a bipolar arrangement during the coagulation process. Due to the fact that cutting electrode 50 is then attached as a third electrode to electrosurgical instrument 10, the holding element, in this case therefore the coagulation electrodes, must be formed in such a manner that a bipolar arrangement with the cutting electrode can also be achieved during the cutting process.

In principle, holding elements 30, 40 can also be formed as electrically insulating elements and would thus only act to fix the tissue to be treated. Cutting electrode 50 as a different electrode would then form a monopolar arrangement together with an indifferent neutral electrode (not shown) to be attached to the patient. With regard to the precise configuration of such arrangements, reference is made to the following description of the figures.

Electrosurgical instrument 10 shown in FIG. 1 is, as already mentioned above, formed for use on the opened body. The principle of cutting electrode 50 according to the invention can also be applied to endoscopy, e.g. in the case of laparoscopic instruments. Holding elements 30, 40 fastened on branches 15, 16 and cutting electrode 50 must then, for example, be activated via a handle fastened on a shaft or a control unit is provided so that an activation of the holding elements and the cutting electrode is controlled via these.

Figure 2:
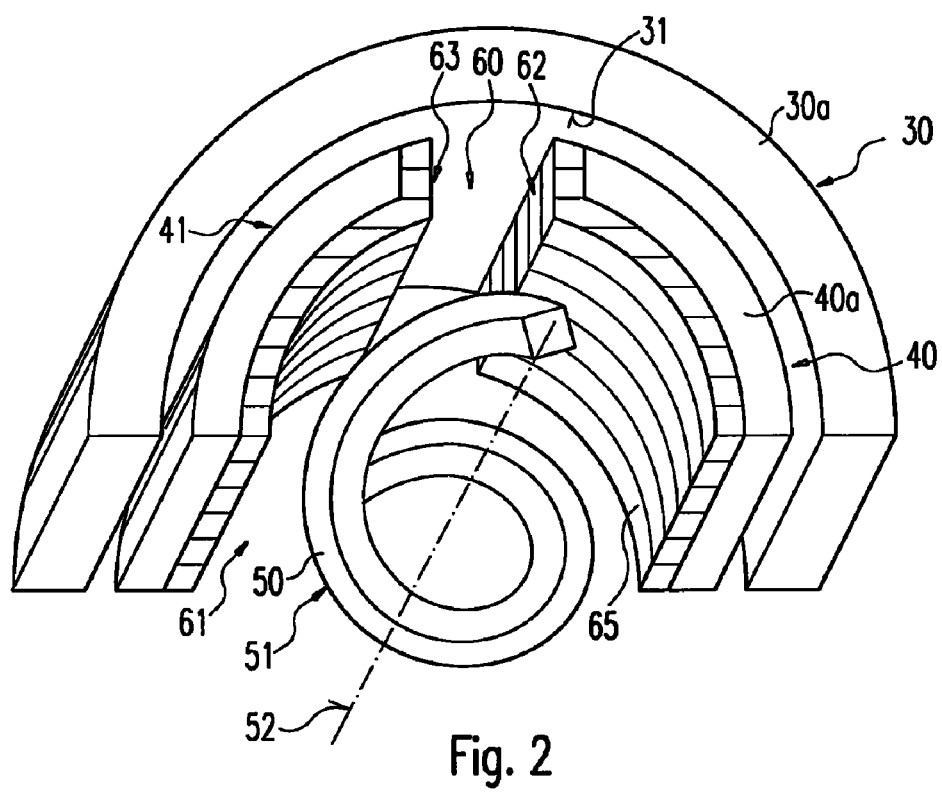
FIG. 2 shows a perspective view of a holding element and/or electrode arrangement according to the first preferred embodiment.

FIG. 2 shows a greatly enlarged perspective view of a holding element and/or electrode arrangement according to the first preferred embodiment as is also apparent from FIG. 1. In this exemplary embodiment, holding elements 30, 40 are formed as coagulation electrodes, i.e. as first coagulation electrode 30a and as second coagulation electrode 40a, in such a manner that first electrode 30a reverse is put over, i.e. covers, second electrode 40a when branches 15, 16 are brought together. As is apparent from the figure, electrodes 30a, 40a are formed in a curved manner. Therein, second electrode 40a comprises a convex curve and first electrode 30a, which lies opposite electrode 40a formed in a convex manner, comprises a concave curve. In this manner, electrodes 30a, 40a fit into one another in a substantially positive-locking manner when branches 15, 16 are brought together. The tissue is pulled, i.e. extended or tightened, by curved electrodes 30a, 40a in the direction of end areas of electrodes 30a, 40a. Electrodes 30a, 40a accordingly form tensioning areas 31, 41. This enables more precise cutting of the tissue since fibres of the tissue are aligned trans-verse to a cutting direction and the tissue becomes thinner in the process. As a result of the positive locking, the tissue is then fixed between electrodes 30a, 40a in a tensioned state. In this exemplary embodiment, electrodes 30a, 40a are substantially entirely formed as tensioning areas 31, 41. Alternatively, it is possible that only sections of the electrodes form tensioning areas.

Alternatively, the tensioning areas can be formed with different radii of curvature; the radius of curvature of the tensioning area formed in a concave manner is, for example, larger than the radius of curvature of that formed in a convex manner. The curves then run about longitudinal axes of the distal ends such that the tissue held between the distal ends and running perpendicular to the longitudinal axes is held with pressure which increases towards central sections of the tensioning areas. The clamped tissue is advantageously locked particularly securely between the tensioning areas in this case due to an increasing pressure. A slipping of the gripped tissue out of the electrode parts is thus ruled out. Moreover, a secure closure of the tissue during the coagulation process is achieved at the areas of high pressure brought about by the high clamping force.

According to FIG. 2, cutting electrode 50 is arranged below second electrode 40a, i.e. second electrode 40a is provided between first electrode 30a and cutting electrode 50. Due to this arrangement, it is necessary to enable cutting electrode 50 to access the tissue clamped between the holding elements or between the coagulation electrodes. In practical use, contact-free cutting by means of cutting sparks is provided so that the cutting electrode is arranged so as to only be able to rotate about itself and is otherwise mounted in a stationary manner. Second electrode 40a therefore comprises a receiving/passage area 60, a receiving area 61 being provided for mounting cutting electrode 50, while a passage area 62 enables the cutting spark to access the tissue to be treated. This means that cutting electrode 50 rotates about rotation axis 52 in order to exploit entire cutting area 51, only sections of cutting areas 51 being conveyed to the clamped tissue in such a manner that a voltaic arc can be generated across passage area 62 between cutting electrode 50 and the tissue clamped in the retaining device (holding elements).

Passage area 62 is normally provided as a defined window area 63 or comprises at least defined window area 63. This means that passage area 62 is configured in such a manner that it only exposes a desired tissue area on the clamped tissue. This prevents an undesirable interaction between cutting electrode 50 and tissue at the points of tissue intended for the cutting process. Defined window area 63 enables extremely precise cut guidance because the cut area is precisely delimited. Moreover, the performance of the cut is largely independent of other parameters such as e.g. the set current strength or voltage as a function of the distance of cutting areas 51 of cutting electrode 50 from the tissue to be treated.

If, however, for example, the HF cutting current or the voltage is controlled such that the active section of cutting area 51 is active on the tissue when it falls below a defined minimum distance to the tissue, receiving/passage area 60 must be configured in such a manner that an obstruction of cutting electrode 50 is prevented by the retaining device. Despite this, a sufficient fixing of the tissue must be ensured.

During the coagulation process, first coagulation electrode 30a and second coagulation electrode 40a act as a bipolar arrangement, cutting electrode 50 preferably being electrically neutral. During the cutting process, cutting electrode 50 would however interact with second electrode 40a via receiving/passage area 60 and bring about an uncontrolled sparking. In order to prevent such undesired effects, second electrode 40a therefore comprises an insulation layer 65 on surface areas which are formed in the direction of cutting electrode 50. This means that receiving/passage area 60 is substantially fitted with insulation layer 65. During cutting, first electrode 30a and cutting electrode 50 then form the bipolar arrangement.

FIG. 2 shows that cutting electrode 50 encompasses a helical line-shaped rod element, cutting area 51 is formed as a helical curve on the rod element and the section of cutting area 51 along the helical curve runs along the rod element when cutting electrode 50 rotates. The rod element is provided to rotate about rotation axis 52. Therein, the rod element can be wound in such a manner that the section of cutting area 51 runs along a surface of the cutting area or along an edge. If the section runs along the edge, a higher current density can be achieved on said section.

Figure 3:
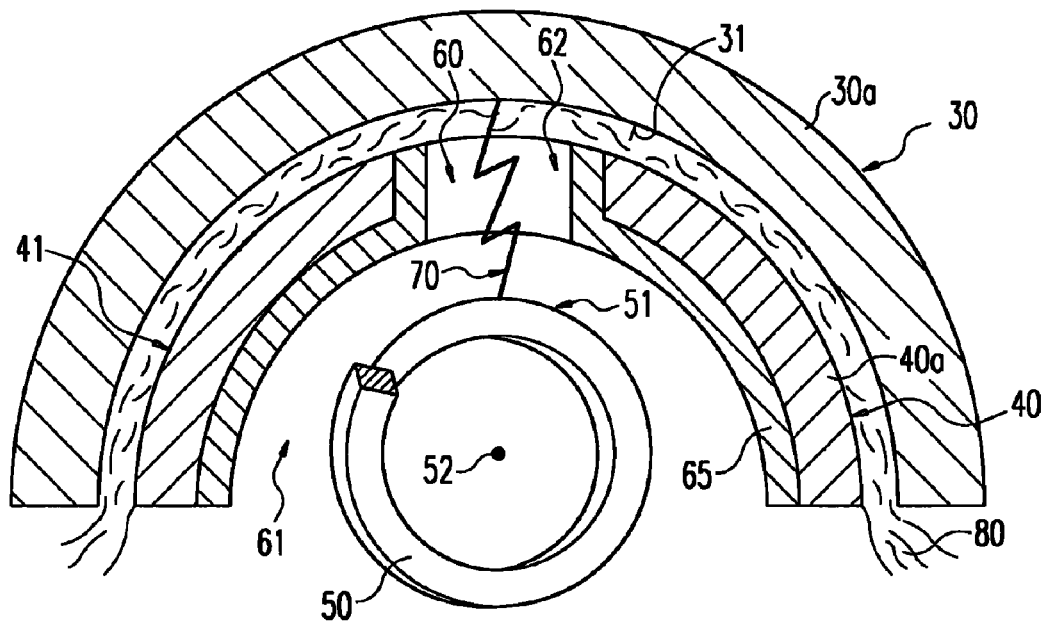
FIG. 3 shows a schematic sectional view of a holding element and/or electrode arrangement in a front view according to the first preferred embodiment.

FIG. 3 shows the holding element and/or electrode arrangement according to FIG. 2 in a sectional front view, the tissue 80 to be treated being clamped between first coagulation electrode 30a and second coagulation electrode 40a. Clamped tissue 80 is separated by means of cutting sparks 70.

A second preferred embodiment of the holding element and/or electrode arrangement according to the invention is shown in FIG. 4. Holding elements 30, 40 are also formed in a curved manner in this case so that the tissue to be treated can be clamped between holding elements 30, 40. FIG. 4 shows that cutting electrode 50 encompasses a twisted surface element on whose edges two cutting areas 51, 51' are formed as helical curves and the section of respective cutting area 51, 51' along the helical curves runs along the surface element when the cutting electrode rotates. Cutting electrode 50 formed in this manner is extremely stable and therefore withstands mechanical stresses to a large extent. An explicit insulation layer on the surface areas of second holding element 40 facing in the direction of cutting electrode 50 or on receiving/passage area 60 to prevent an interaction between cutting electrode 50 and second holding element 40 is not provided in this case because holding element 40 is e.g. formed as an electrically insulating holding element 40b. The interaction is thus ruled out. In this embodiment, cutting electrode 50 and first electrode 30a form a bipolar arrangement for carrying out the cutting process.

Holding element 40 could alternatively be provided as an electrode so that the receiving/passage area would have to be fitted with the insulation layer.

Furthermore, it is possible as already described under FIG. 1 that both holding elements 30, 40 are formed from electrically insulating material so that the cutting electrode is provided as a single electrode on the electrosurgical instrument. The neutral electrode attached to the patient would then form a monopolar arrangement together with the cutting electrode.

FIG. 5 shows a perspective view of a holding element and/or electrode arrangement according to a third preferred embodiment. The arrangement substantially corresponds to the arrangements shown in FIGS. 2 to 4 and can likewise be formed according to the variants described above. In this exemplary embodiment, however, holding element 40 opposite receiving/passage area 60 comprises a protruding area 32 in the direction of receiving/passage area 60 for conveying the tissue to be treated and/or for introducing the tissue to be treated into receiving/passage area 60. This enables the cut guidance to be specified because e.g. the cutting spark preferably occurs only within passage area 62. Moreover, moisture in the tissue remains for a longer time in passage area 62 so that a required cutting energy can be reduced.

Figure 6:
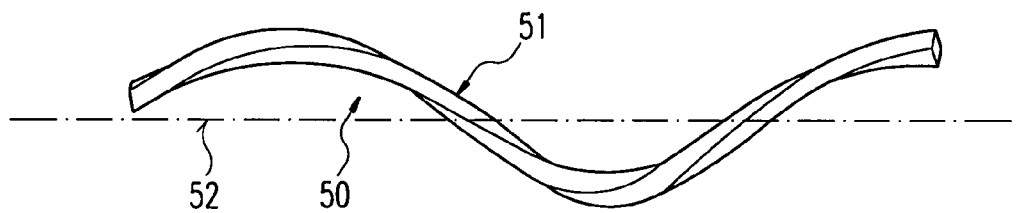
FIG. 6 shows a perspective view of a cutting electrode.
Figure 7:
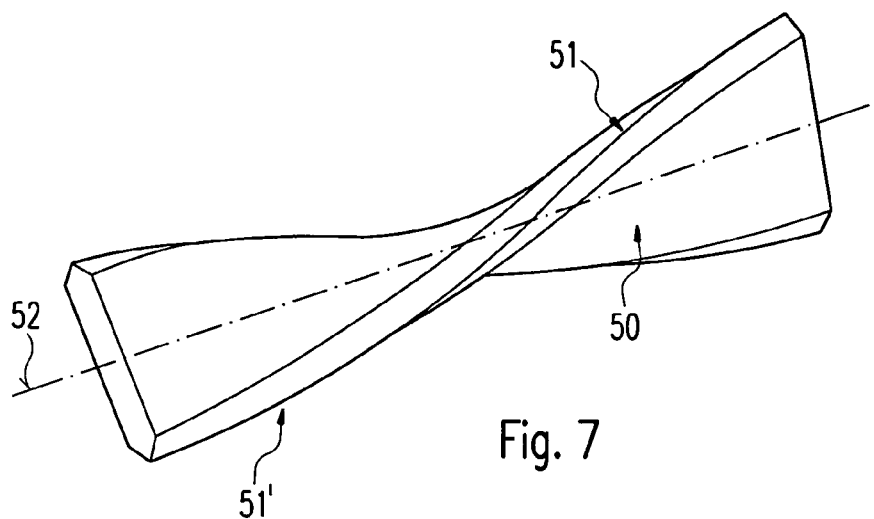
FIG. 7 shows a perspective view of a cutting electrode.

FIGS. 6 and 7 respectively show cutting electrodes 50 individually, as already described by FIGS. 2 to 5.

Figure 8:
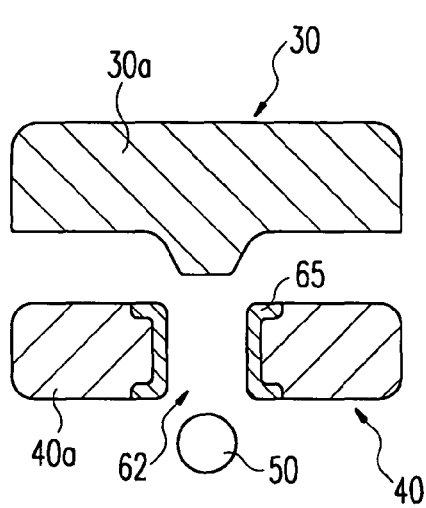
FIG. 8 shows a schematic sectional view of a holding element and/or electrode arrangement in a front view according to a fourth preferred embodiment.
Figure 9:
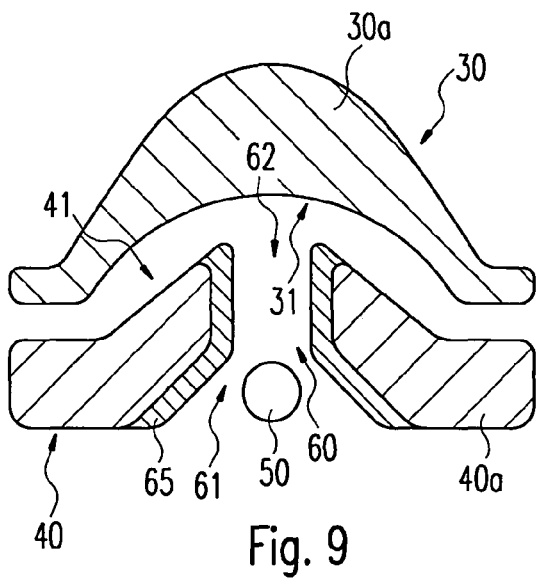
FIG. 9 shows a schematic sectional view of a holding element and/or electrode arrangement in a front view according to a fifth preferred embodiment.
Figure 10:
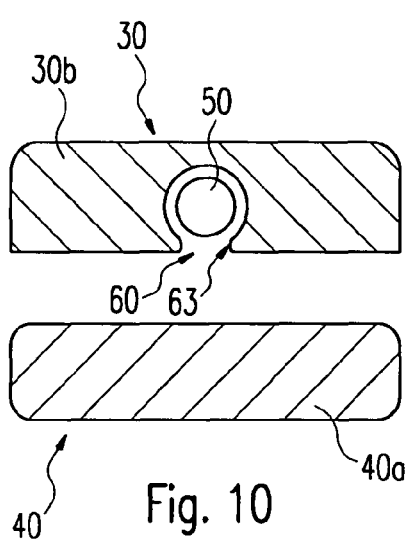
FIG. 10 shows a schematic sectional view of a holding element and/or electrode arrangement in a front view according to a sixth preferred embodiment.
Figure 11:
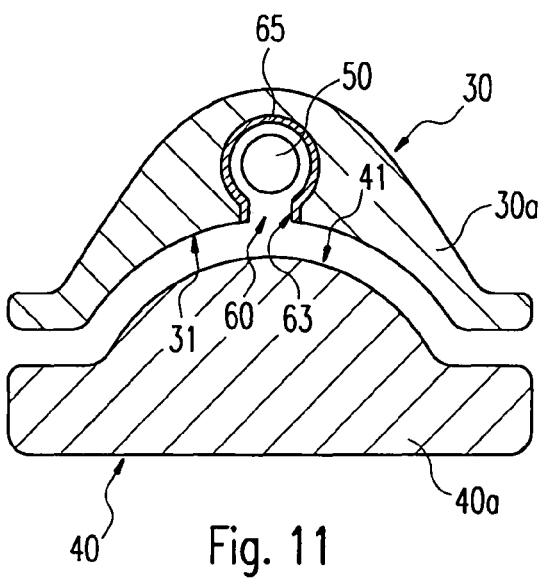
FIG. 11 shows a schematic sectional view of a holding element and/or electrode arrangement in a front view according to a seventh preferred embodiment.

Further holding element and/or electrode arrangements are shown in FIG. 8 with a fourth preferred embodiment, in FIG. 9 with a fifth preferred embodiment, in FIG. 10 with a sixth preferred embodiment and in FIG. 11 with a seventh preferred embodiment. The drawings show the holding element and/or electrode arrangements from the front but in a schematic section. It should be mentioned that the holding elements shown in the Figs., as already describe above, can respectively be formed as coagulation electrodes and/or as electrically insulating elements.

FIG. 8 shows holding elements 30, 40 with a substantially rectangular cross-section in terms of the outer form. The holding elements are, for example, formed as first coagulation electrode 30a and as second coagulation electrode 40a. Second electrode 40a comprises receiving/passage area 60 for cutting electrode 50, receiving/passage area 60 substantially consisting of passage area 62 in this case. Cutting electrode 50, indicated here as a circle, is accordingly mounted below second electrode 40a. In order to prevent interaction between cutting electrode 50 and second electrode 40a, second electrode 40a comprises insulation layer 65 on receiving/passage area 60 on the surface areas which substantially face cutting electrode 50. Cutting electrode 50 and first electrode 30a thus form the bipolar arrangement during the cutting process. First electrode 30a comprises a protruding area in the direction of receiving area 61 for conveying the tissue to be treated and/or for introducing the tissue to be treated into receiving area 61.

The arrangement of holding elements 30, 40 and cutting electrode 50 according to FIG. 9 substantially corresponds to that from FIG. 8. In this case too, the holding elements are formed as first coagulation electrode 30a and as second coagulation electrode 40a, but have a curved shape and therefore tensioning areas 31, 41 described above for fixing and tightening the tissue to be treated. Receiving/passage area 60 is formed funnel-shaped in the direction of a side facing away from holding surfaces of holding elements 30, 40 so that cutting electrode 50 is accommodated in a protected manner within the second electrode.

FIG. 10 in turn shows holding elements 30, 40 which substantially comprise a rectangular cross-section. Due to the fact that cutting electrode 50 is formed here between first holding element 30 and second holding element 40, receiving/passage area 60 is located here, for example, within first holding element 30. In this case, the first holding element is formed as an electrically insulating element 30b and the second holding element as coagulation electrode 40a so that cutting electrode 50 forms the bipolar arrangement with second electrode 40a.

FIG. 11 substantially corresponds to FIG. 10, the holding elements here being formed as first coagulation electrode 30a and as second coagulation electrode 40a and comprising tensioning areas 31, 41. Receiving/passage area 60 is arranged within first electrode 30a so that it is fitted with insulation layer 65. This prevents interaction of cutting electrode 50 with first electrode 30a during the cutting process.

Irrespective of the configuration of the holding elements, cutting electrode 50 can itself respectively be formed as a helical curve or similar three-dimensional curve running around rotation axis 52, therefore e.g. as a wound rod element or as a twisted sheet or, for example, encompass the wound rod element.

Receiving/passage areas 60 shown in the Figs. are preferably configured from their dimensions in such a manner that they form defined window area 63. It is thus constantly ensured that only a defined tissue area is accessible for the cutting process.

Figure 12:
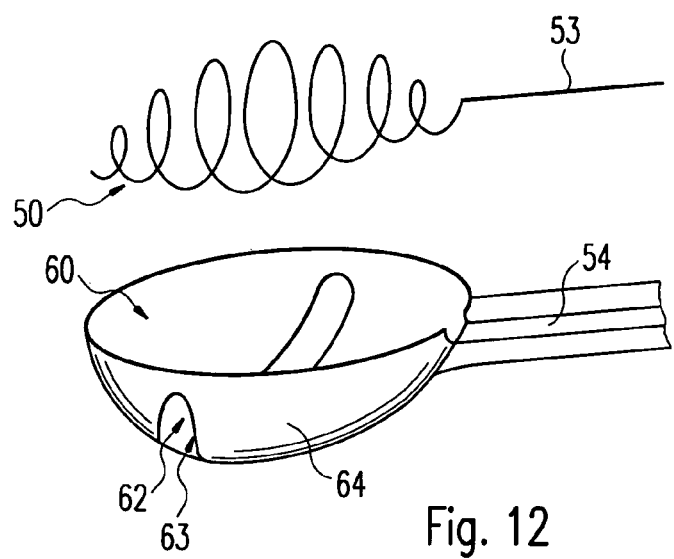
FIG. 12 shows a perspective view of an electrode arrangement according to an eighth preferred embodiment.

Other shapes can also be provided for the cutting electrode and the receiving/passage area. In particular, the receiving/passage area can be formed on or in an additional, possibly exchangeable element on the electrosurgical instrument, i.e. an electrosurgical arrangement comprises, as well as the electrodes, an explicit element for the receiving/passage area (a predefined window area can thus e.g. be varied). Element 64 can, however, also be formed only as a curved holding element, as has already been described with the exemplary embodiments above. FIG. 12 thus shows a schematic view of a wound cutting electrode 50, which substantially describes the envelope of a rotational ellipsoid. Electrode 50 must, for example, be arranged in correspondingly trough-shaped element 64 for receiving/passage area 60, element 64 being formed e.g. as an electrically insulating element or even as an electrode. Depending on the embodiment, a neutral electrode or a further electrode (not shown) which can be put over trough-shaped element 64 can be provided as the counter electrode so that the tissue to be treated is clamped between element 64 and the further electrode. Passage area 62 is preferably formed as defined window area 63. Due to trough-shaped elements 64, window area 63 is formed in a curved manner such that, for example, a precise cut can be performed along the curved window area. Cutting electrode 50 is rotated by means of the rotational drive and a drive shaft 53 mounted in a guide 54 of the element.

At this point, it should be noted that all the above-mentioned parts are claimed as essential to the invention by themselves or in any combination, in particular the details shown in the drawings. Modifications of these are familiar to the person skilled in the art.

LIST OF REFERENCE NUMBERS

10 Electrosurgical instrument
11 Distal end
12 Distal end
13 Proximal end
14 Proximal end
15 Branch
16 Branch
17 Axis
18 Handle
19 Handle
20 Power connection element, power supply device
21 Rotational drive
21' Finger wheel
30 First holding element
30a First coagulation electrode
30b Electrically insulating element
31 Tensioning area
40 Second holding element
40a Second coagulation electrode
40b Electrically insulating element
41 Tensioning area
50 Cutting electrode
51 Cutting area
51' Cutting area 52 Rotation axis
53 Drive shaft
54 Guide
60 Receiving/passage area
61 Receiving area
62 Passage area
63 Defined window area
64 Element for the receiving/passage area
65 Insulation layer
70 Voltaic arc, cutting spark
80 Tissue

The invention claimed is;

1. An electrosurgical instrument for cutting and coagulating a tissue to be treated comprising:
    at least one cutting electrode for conducting a high-frequency current through the tissue for carrying out a cutting process; and
    power supply devices for supplying the high-frequency current at least to the at least one cutting electrode,
    wherein the at least one cutting electrode is mounted on the electrosurgical instrument in a manner that enables the at least one cutting electrode to rotate about a rotation axis, the at least one cutting electrode comprising at least one cutting area which is provided in the form of a helical curve running around the rotation axis and which is arranged in such a manner that when the at least one cutting electrode rotates about the rotation axis the at least one cutting electrode is active in sections over its length, each section acting on the tissue when the section falls below a defined minimum distance from the tissue or is located within a defined window area;
    further comprising two branches which are connected to one another and which can be activated according to a clamping or cutting tool and thus form a retaining device that includes at least one holding element on the branches for holding the tissue to be treated, the at least one holding element including a receiving/passage area comprising a receiving area and a passage area such that the at least one cutting electrode can be mounted in or on the holding elements in the receiving area and a voltaic arc can be generated across the passage area between the at least one cutting electrode and the tissue clamped in the retaining device, wherein the at least one cutting electrode encompasses a twisted surface element on whose edges two cutting areas are formed as helical curves and the section of the cutting areas along the helical curves runs along the surface element when the cutting electrode rotates.

2. The electrosurgical instrument according to claim 1, wherein the twisted surface element is a helical line-shaped rod element.

3. The electrosurgical instrument according to claim 1, wherein the at least one cutting electrode includes at least one turn.

4. The electrosurgical instrument according to claim 1, wherein the receiving/passage area comprises the defined window area.

5. An electrosurgical instrument for cutting and coagulating a tissue to be treated comprising:
    at least one cutting electrode for conducting a high-frequency current through the tissue for carrying out a cutting process; and
    power supply devices for supplying the high-frequency current at least to the at least one cutting electrode,
    wherein the at least one cutting electrode is mounted on the electrosurgical instrument in a manner that enables the at least one cutting electrode to rotate about a rotation axis, the at least one cutting electrode comprising at least one cutting area which is provided in the form of a helical curve running around the rotation axis and which is arranged in such a manner that when the at least one cutting electrode rotates about the rotation axis the at least one cutting electrode is active in sections over its length, each section acting on the tissue when the section falls below a defined minimum distance from the tissue or is located within a defined window area;
    further comprising two branches which are connected to one another and which can be activated according to a clamping or cutting tool and thus form a retaining device that includes at least one holding element on the branches for holding the tissue to be treated, the at least one holding element including a receiving/passage area comprising a receiving area and a passage area such that the at least one cutting electrode can be mounted in or on the holding elements in the receiving area and a voltaic arc can be generated across the passage area between the at least one cutting electrode and the tissue clamped in the retaining device, wherein the retaining device comprises a first electrode and a second electrode for conducting a coagulation current for the coagulation process through the tissue, the first and second electrodes being holding elements respectively on the branches.

6. The electrosurgical instrument according to claim 5, wherein the receiving/passage area comprises an insulation layer on at least surface areas facing in the direction of the at least one cutting electrode so that the first or second electrode which is opposite the first or second electrode comprising the receiving/passage area and the at least one cutting electrode form a bipolar arrangement during the cutting process.

7. The electrosurgical instrument according to claim 1, wherein the retaining device comprises an electrode and an electrically insulating holding element, the electrode and the at least one cutting electrode being arranged relative to one another in such a manner that they form a bipolar arrangement during the cutting process.

8. The electrosurgical instrument according to claim 1, wherein the at least one holding element is opposite the receiving/passage area and comprises a protruding area in the direction of the receiving/passage area for conveying the tissue to be treated or for introducing the tissue to be treated into the receiving/passage area.

9. The electrosurgical instrument according to claim 1, wherein the at least one holding element respectively comprises at least one tensioning area in such a manner that, during clamping of the tissue, the tissue is pretensioned between the holding elements and the cutting process can be performed by means of the cutting electrode on the pretensioned tissue.

10. The electrosurgical instrument according to claim 9, wherein the at least one tensioning area is curved in a convex manner at least in a first central section, while a second tensioning area opposite the at least one tensioning area is curved in a concave manner at least in a second central section so that the at least one tensioning area and second tensioning area fit into one another in a substantially positive-locking manner when the branches are brought together.

11. The electrosurgical instrument according to claim 1, wherein a rotational drive for rotating the cutting electrode is assigned to the electrosurgical instrument.

* * * * *